US009880156B2

(12) United States Patent
Jolley et al.

(10) Patent No.: US 9,880,156 B2
(45) Date of Patent: Jan. 30, 2018

(54) BIOLOGICAL SPECIMEN EVALUATION METHODS USING CYTOLOGY AND IMMUNOLOGY

(71) Applicant: CYTOCORE, INC., Orlando, FL (US)

(72) Inventors: Michael E. Jolley, Round Lake, IL (US); Richard A. Domanik, Libertyville, IL (US)

(73) Assignee: Medite Cancer Diagnostics, Inc., Orlando, FL (US)

( * ) Notice: Subject to any disclaimer, the term of this patent is extended or adjusted under 35 U.S.C. 154(b) by 136 days.

(21) Appl. No.: 14/774,988

(22) PCT Filed: Apr. 1, 2014

(86) PCT No.: PCT/US2014/032563
§ 371 (c)(1),
(2) Date: Sep. 11, 2015

(87) PCT Pub. No.: WO2014/168788
PCT Pub. Date: Oct. 16, 2014

(65) Prior Publication Data
US 2016/0033482 A1    Feb. 4, 2016

Related U.S. Application Data

(60) Provisional application No. 61/811,034, filed on Apr. 11, 2013.

(51) Int. Cl.
| | | |
|---|---|---|
| G01N 33/53 | (2006.01) | |
| G01N 33/58 | (2006.01) | |
| G01N 33/50 | (2006.01) | |
| G01N 33/68 | (2006.01) | |
| G01N 33/574 | (2006.01) | |

(52) U.S. Cl.
CPC ..... *G01N 33/5091* (2013.01); *G01N 33/5023* (2013.01); *G01N 33/5026* (2013.01); *G01N 33/57496* (2013.01); *G01N 33/6869* (2013.01); *G01N 2333/525* (2013.01); *G01N 2333/5428* (2013.01); *G01N 2333/715* (2013.01); *G01N 2800/50* (2013.01); *G01N 2800/7028* (2013.01); *G01N 2800/7095* (2013.01)

(58) Field of Classification Search
CPC .............................. G01N 33/58; G01N 33/582
See application file for complete search history.

(56) References Cited

U.S. PATENT DOCUMENTS

| | | | |
|---|---|---|---|
| 6,007,996 A | 12/1999 | McNamara et al. | |
| 6,087,088 A | 7/2000 | Piran et al. | |
| 7,510,838 B2 | 3/2009 | Fischer et al. | |
| 2012/0264110 A1 | 10/2012 | Wachman et al. | |

FOREIGN PATENT DOCUMENTS

| WO | WO 02/42267 | 5/2002 |
|---|---|---|
| WO | WO 2010/118166 | 10/2010 |

OTHER PUBLICATIONS

El-Sherif, A.M., et al., Journal of Pathology, 192: 494-501, 2000.*
Bock, H., Appl. Phys. B, 88:162-165, 2007.*
Azar, K. K., et al., Hum. Phathol. 35: 1376-1384, 2004.*
Sander, B., et al., Immunological Reviews, 119: 65-93, 1991, "Assessment of Cytokines by Immunofluorescence and the Paraformaldehyde-Saponin Prodedure", Munksgaard, Copenhagen, Denmark.*
Mindiola et al., "Increased number of IL-2, IL-2 receptor and IL-10 positive cells in premalignant lesions of the cervix", *Investigacion Clinica*, 49(4): 533-545 (2008).
Punyani et al., "Salivary level of interleukin-8 in oral precancer and oral squamous cell carcinoma," *Clin. Oral Invest.*, 17:517-524 (2013).
Supplementary Partial Search Report issued in EP App. No. 14783232 (dated Aug. 11, 2016).
Maker et al., "Cyst Fluid Interleukin-1β (IL1β) Levels Predict the Risk of Carcinoma in Intradcutal Papillary Mucinous Neoplasms of the Pancreas," *Clin. Cancer Res.*, 17(6): 1502-1508 (2011).
Mindiola et al., "Increased number of IL-2, IL-2 receptor and IL-10 positive cells in premalignant lesion of the cervix," *Invest. Clin.*, 49(4): 533-545 (2008).
Scott et al., "Cell-Mediated Immune Response to Han Papillomavirus Infection," *Clin. Diag. Lab. Immunol.*, 8(2): 209-220 (Mar. 2001).
Search Report and Written Opinion issue in Int'l App. No. PCT/US2014/032563 (2014).

* cited by examiner

*Primary Examiner* — Jeffrey J Stucker
*Assistant Examiner* — Anne L Holleran
(74) *Attorney, Agent, or Firm* — Barnes & Thornburg LLP; Alice O. Martin

(57) ABSTRACT

Information on cytokines and cytology obtained from a biological specimen are combined as a method of predicting the risk that dysplasia will progress to cancer. Methods are disclosed herein to augment the evaluation of biological samples from subjects being tested for cancer. In addition to the cell types that are traditionally considered in the morphology-based cytological screening of specimens, methods disclosed herein add evaluations of certain cell types and cytokines that are traditionally discounted or ignored during screening.

3 Claims, 4 Drawing Sheets

BIOLOGICAL SPECIMEN EVALUATION METHODS USING CYTOLOGY AND IMMUNOLOGY

CROSS REFERENCE TO RELATED APPLICATIONS

This application is a U.S. nationalization under 35 U.S.C. § 371 of International Application No. PCT/US2014/032563, filed Apr. 1, 2014, which claims the benefit of U.S. provisional application 61/811,034 filed Apr. 11, 2013. The disclosures set forth in the referenced applications are incorporated herein by reference in their entireties.

BACKGROUND

Information on cytokines and cytology obtained from biological specimens are combined in methods of predicting the risk that dysplasia will progress to cancer.

1. Screening for Dysplasia

A well known problem in clinical medicine is that, although precancerous lesions (dysplasias) are relatively common, only a small proportion of these lesions progress to actual cancer. In the absence of a reliable means to differentiate between lesions that are likely to progress to cancer and those that are not, clinicians generally take a conservative approach and aggressively treat all lesions that exceed some threshold of abnormality. One disadvantage of such a conservative approach is that a significant fraction of these patients receive unnecessary and/or excessively aggressive treatments, many of which are known to produce serious side effects. A second disadvantage is that such unnecessary treatments consume large amounts of limited medical resources, thereby diverting these resources from other patients who could derive more benefit from them. Thus there is a need for a means to differentiate between precancerous lesions that are likely to progress to cancer and those that are not.

Disease screening programs present a challenge in that the tests used must be capable of quickly, accurately and efficiently examining large numbers of asymptomatic individuals in order to detect those few who exhibit subclinical indications of having the disease or a precursor condition. In other words, disease screening is an exercise in rare event detection in which the test used must be sensitive enough to detect subclinical manifestations of the disease and specific enough to accurately differentiate these manifestations from similar manifestations resulting from other causes. An additional complication, particularly in the area of cancer screening, is that once initiated, the disease does not always progress to the point of becoming symptomatic, but may stop at some point or even regress back to normal.

Cervical cancer screening and the subsequent follow up to abnormal screening results provide what is arguably the best documented example of the success of cancer screening. Similar to most screening tests, cervical cancer screening is performed on large asymptomatic patient populations with the intent of identifying those few members of these populations who could benefit from treatment or other appropriate intervention. Because large numbers of asymptomatic individuals must be screened in order to identify the few that exhibit the target disease state, logistics and economics play crucial roles in the deployment and operation of screening programs In particular, the large number of individuals to be screened dictates that the logistics of sample collection and testing be highly efficient. The high costs associated with the confirmation of an abnormal screening result and the even higher costs of treatment (if the abnormal result is confirmed) also impose stringent requirements on the screening process including that the screening test be highly specific and that the costs of screening be minimized.

Since the mid-1940's, cervical cancer screening has been performed using the Pap test, in which cells collected from each individual are examined cytologically to identify those samples that contain cells that exhibit the morphological abnormalities that indicate the presence of dysplasia or cancer. Patients from whom cytologically abnormal specimens are obtained receive follow up, typically by the histological examination of tissue samples obtained by biopsy, in order to confirm the presence of the abnormality and, if confirmed, to diagnose the specific disease state that is present. This diagnosis, in turn, provides the basis for treatment planning and delivery.

At present, cervical cancer screening is based upon the morphological evaluation of squamous epithelial cells and, in some cases, endocervical cells, obtained from the cervix. In the original form of this test these were cells that had been exfoliated from the cervix, but since the late 1940's they have been obtained by scraping the cervix with a spatula, brush or broom device. The major reason for this change in sample collection method was to obtain a "cleaner" sample that is enriched in the cervical squamous epithelial cells to be morphologically evaluated. Until the early 1990's these samples were typically smeared onto a microscope slide in preparation for cytological evaluation. Although this slide preparation method is simple and effective, the resulting specimens often contain clusters and clumps of cells, mucus, bacteria, fungi, yeasts, and non-epithelial cells that can impair the examination of the epithelial cells of clinical interest.

In the late 1990's smears began to be displaced by "monolayer" (or "liquid based") preparations that facilitate specimen evaluation by better dispersing the epithelial cells, while eliminating or significantly reducing the amount of mucus and the numbers of non-epithelial cells on the slide by means of a purification step in the slide preparation procedure. At the present time these monolayer preparations, which are endorsed by medical societies and National Health Authorities worldwide, account for over 80% of the cervical screening specimens in the US and UK, and comprise a significant, and growing, fraction of the cervical screening specimens worldwide.

Statistics published by the World Health Organization indicate that the incidence rate of cervical cancer varies by country and is generally in the range of 0.02 to 0.1%. The Pap test is by far the predominant method used in cervical cancer screening worldwide. In this test cells squamous epithelial cells collected from the cervix are cytologically examined, and any morphological abnormalities observed in these cells are classified in accordance with internationally accepted criteria (the Bethesda criteria). These categories are:

(a) Within Normal Limits (WNL): no significant abnormalities noted (b) Atypical Squamous Cells of Undetermined Significance (ASCUS): a category used primarily in the US for cells exhibiting relatively minor morphological abnormalities that do not fall into the other classifications.

(c) Low Grade Squamous Interepithelial Lesion (LSIL or LGSIL): moderate morphological abnormalities consistent with dysplasia. Cells exhibiting morphological changes consistent with viral infection may also be included in this category.

(d) High Grade Squamous Interepithelial Lesion (HSIL or HGSIL): severe dysplastic morphological abnormalities. This is the level at which standards of care generally prescribe aggressive medical intervention.

(e) Cancer.

Although the numbers vary somewhat by patient population, a realistic approximation is that in developed countries, the outcome of a cervical cancer screening program will consist of approximately 90% WNL; 9% ASCUS+LSIL; 0.9% HSIL and 0.1% cancer. These numbers indicate that only a small percentage of cervical dysplasias actually progress to cervical cancer. This is supported by the well established observation that most dysplasias are spontaneously cleared by the body without the need for therapeutic intervention. A means of reliably predicting which dysplasias are likely to progress to cancer is needed in order to optimally use scarce medical resources. It is also well established that when biopsy is used for confirmation, the sensitivity (% of dysplasias detected)

Specificity is the percent of normals correctly identified as such; the false positive rate is 1-specificity.

From an operational perspective, a sensitivity of 70% means that approximately one third of the individuals in the population being screened who have cervical dysplasia or cervical cancer are not detected by the Pap test. From this it is obvious that there is a need to increase the sensitivity of the test that is used for cervical cancer screening. Similarly, a specificity of 70% means that approximately one third of the cases classified by the test as having dysplasia or cancer cannot be confirmed and are generally reclassified as being WNL. In addition to the emotional effects of such an erroneous classification, these false positive results have a significant economic impact as the follow up testing needed to identify the true positive cases within this group is far more expensive in terms of the money and medical resources required than is the initial screening. Given the severe constraints on the availability of healthcare resources worldwide, expending resources on following up on a false positive screening result means that fewer individuals can be screened and that fewer resources are available for the treatment of individuals who are truly positive for dysplasia or cancer. There is need for improving the specificity of the cervical cancer screening test.

Although the preceding description focused on cervical cancer screening, these and other similar considerations and needs identified apply to screening programs for other cancers such as, but not limited to those of breast, prostate, lung and bladder.

Previous attempts to improve sensitivity and specificity have focused upon the development of assays for the detection of "markers" that can be correlated with the presence of dysplasia, improved methods of morphological evaluation, and the use of surrogate indicators. Markers are cell surface or intracellular molecules whose concentrations significantly increase or decrease if cellular processes are disrupted. The markers that have been used to date have almost exclusively been proteins, but the use of a small number of other types of molecules such as lipids and oligonucleotides has occasionally been explored. Although many of these marker-based tests offer high sensitivity, their specificities tend to be limited due to the fact that these markers are normal constituents of cells and play roles in normal and routine cellular processes. These markers are also not expressed in isolation, but rather as elements of a highly interconnected network of cellular processes wherein the factors causing a change in the expression of one marker can have diverse effects on the expression of many other markers. The networks involved in routine cellular maintenance and repair have proven to be particularly troublesome in this regard. The most fruitful marker-based approaches to date have focused upon correlation of the expression of multiple markers rather than on the expression of a single marker. Limited success has also sometimes been achieved by precisely quantitating the level of marker expression in individual cells. In addition to the numerous technical challenges of making the necessary quantitative measurements, normal inter-individual and even intra-sample variability makes it extremely challenging to determine the true background or reference level for expression of the marker that is needed in order to determine whether a measured change in expression is significant. Similar challenges and limitations apply to the use of improved methods of morphological evaluation, most of which are based upon various methods of automated image analysis. Repairative cellular processes and the need for unusually stringent process control in the preparation and imaging of the specimen are particularly troublesome and limiting in this approach.

The challenges and limitations described above have led to the exploration of the use of surrogate markers for the detection of cancerous and precancerous conditions. Arguably the best developed of these methods is the use of HPV testing for cervical cancer screening. This use is based upon the strong correlation (>90%) that has been observed between infection by one or more "high risk" (oncogenic) strains of the HPV virus, and HSIL/cancer. The argument presented in favor of this approach is that because the HPV virus itself, and the various proteins and other molecules that it produces in cells, are all "foreign", tests based upon this approach are not subject to many of the limitations outlined above. Although there is a strong correlation between the presence of HPV infection by one or more oncogenic strains and the presence of dysplasias up to and including cancer, it is also well known in the art that only very few such infections actually progress as far as HSIL and even fewer progress to cancer. As a consequence, although HPV tests are highly sensitive, their false positive rates are routinely reported to be in the range of 40-60%. A few reports in the literature have recently suggested that this is a consequence of HPV-induced dysplasias progressing to cancer being not a direct result of the infection itself, but rather being a reflection of relatively rare random errors that can occur during the propagation of the virus within a cell. This, in turn, has led to proposals to use the increased expression of the HPV proteins E6 and E7 that seems to be better correlated with HSIL and cancer as markers. This approach, however, runs into limitations similar to those described above as expression of E6 and E7 is a normal part of the HPV life cycle and is therefore not in and of itself definitive for cells that will progress to cancer.

As long ago as the 1850's it was observed that tumors in some cancer patients who acquired and then recovered from certain life threatening infections, shrank or even completely disappeared. It was also observed that a substantial portion, over 50% in some cases, of the mass of a solid tumor was comprised of white blood cells. More recently it was determined that these tumor-infiltrating lymphocytes (TIL's) consist primarily of T-cells, NK cells, dendritic cells, neutrophils, macrophages and other of the types of cells comprising the innate immune system. Other research has demonstrated that a primary function of these cells is to detect, attack and destroy unneeded, damaged, foreign, infected and otherwise abnormal cells.

2. Relevant Aspects of the Human Immune System

Although the structure of the human immune system, its control, and its relationship with cancer, are not yet completely understood, a few points that pertain to the present invention can be summarized as:

(a) The interactions between the immune system and cancer are complex and not well understood. These interactions can range from the immune system attacking and destroying the cancer to entering a state in which the cancer is tolerated, or even actively promoted. There is also a large and growing body of evidence that a developing cancer can modulate the corresponding immune response by any of a number of means.

(b) Newly appearing dysplastic and cancer cells are initially detected and neutralized or destroyed by effector T-cells, NK-cells, macrophages and other cells of the innate immune system. This is typically described as an inflammatory response on the basis of the types of cytokines that are produced.

(c) A B-cell (antibody, humoral) response to the cancer may be generated.

(d) If the cancer is cleared in a timely manner, the immune response reverts to its resting surveillance state, leaving sensitized memory T- and B-cells that can respond rapidly if another similar cancer is subsequently detected.

(e) If the cancer persists and is not cleared in a timely manner, certain cells of the immune system can undergo phenotypic shifts that reduce or terminate the immune response in the vicinity of the cancer. Among the shifts that have been reported:

Helper T-cells transition from the Th1 phenotype (expressing pro-inflammatory cytokines and promoting an immune response) to the Th2 phenotype (expressing anti-inflammatory cytokines and suppressing the immune response).

A portion of the T-cell population adopts a regulatory (Treg) phenotype that can locally suppress the innate immune response. Less is known about regulatory B-cells (Bregs) that appear to be generated before, or at the same time as Tregs, and locally suppress the immune response.

A portion of the local macrophage population transitions from Type M1 (aggressive) to Type M2 (tolerant).

Th2 helper T-cells, Tregs, M2 macrophages and Bregs secrete anti-inflammatory cytokines that, in addition to locally suppressing the local immune response, can promote angiogenesis and other aspects favorable to tumor proliferation.

Cancer cells can express anti-inflammatory cytokines including, but not limited to, Interleukin-10 (IL-10). Certain of these cytokines, most notably IL-10, down-regulate the cancer-specific immune response by suppressing Interferon Gamma (IFN-γ), IL-2 and IL-12 production. This results in an increased production of other anti-inflammatory cytokines such as IL-4 and IL-6, a reduced display of tumor antigens by the Major Histocompatibility Complex (MHC) on the surfaces of tumor cells, and the inhibition of the presentation of tumor-specific antigens by dendritic and other antigen-presenting cells.

Certain cells of the innate immune system, most notably T-cells and NK cells, individually examine the cell surface markers displayed by the cells comprising the tissues in their vicinity to determine their status. Detection of a cell that displays an abnormal suite of these markers triggers a cytolytic and cytotoxic response from the T- or NK cell that is directed at destroying the abnormal cell. At the same time these cells release a variety cytokines and chemokines that attract macrophages, neutrophils, dendritic cells and other cells of the innate immune system to the site and activate them to continue the destruction of the abnormal cell and to remove the resulting debris. Certain interferons and other molecules that interact directly with the target cell may also be released. The destruction of an abnormal cell therefore usually proceeds rapidly and efficiently, but is in some cases not sufficient to completely eliminate a lesion.

It is reported, primarily from research into the genesis of autoimmune diseases, that an overly prolonged inflammatory immune response of the type described above can result in the activated immune cells damaging and subsequently attacking normal cells in the vicinity of the original lesion. In order to prevent this type of undesirable collateral damage, a highly effective means of terminating the inflammatory immune response is provided and is triggered either when the target cell is destroyed or if the inflammatory response is excessively prolonged. Just as the attack phase of the immune response is largely mediated by pro-inflammatory cytokines, the termination phase is largely mediated by anti-inflammatory cytokines with the balance between them being controlled by a complex network of interactions between the various types of immune cells that are present. Recently research into the use of activated T-, NK and dendritic cells as cancer therapeutic agents has revealed that the balance between pro- and anti-inflammatory cytokines can also be modulated by the target cells themselves. In particular it has been found that in many cases dysplastic and cancerous cells are capable of expressing and releasing sufficient quantities of anti-inflammatory cytokines to suppress or terminate the immune attack upon them and to locally force the innate immune system into a quiescent state Imposition of this local immunosuppressed state is thought to be necessary and sufficient to permit progression of the dysplasia or cancer.

SUMMARY OF THE DISCLOSURE

Methods are disclosed herein to augment the evaluation of biological samples from subjects being tested for cancer. In addition to the cell types that are traditionally considered in the morphology-based cytological screening of specimens, methods disclosed herein add evaluations of certain cell types and cytokines that are traditionally discounted or ignored during screening.

Target cells are the cell types that are scored as "normal", "dysplastic" or "cancerous." For example, epithelial cells are generally the target cells for cervical cancer screening.

Among the cell types that are eliminated from, or substantially reduced in number, in monolayer specimen preparations are lymphocytes (T-cells and B-cells), neutrophils, dendritic cells and macrophages. Although these cell types, if present in large numbers in smear specimens, have occasionally been reported as indicators of infections such as vaginitis, they have historically been ignored with respect to cervical cancer screening. It is these historically and intentionally ignored cells and certain cytokines associated with them, that are the basis of the disclosed materials and methods claimed herein.

Methods and compositions are disclosed to monitor the status of the innate immune system in the region from which the biological sample was collected, to determine whether the immune system is locally suppressed and, if so, whether this suppression is being imposed or reinforced by dysplastic or cancer cells. Several possible general outcomes, each of which carries a different risk of progression, can be envisioned:

1. A normal state is indicated by the absence of dysplastic/cancerous cells and the absence of cells expressing anti-inflammatory cytokines.
2. A normal immune response is suggested if dysplastic or cancerous cells are present, but neither immune nor target cells are expressing anti-inflammatory cytokines. This can indicate a slightly elevated risk.
3. A suppressed immune response is indicated if immune cells expressing anti-inflammatory cytokines are present. If the target cells that are present are morphologically normal, and not expressing anti-inflammatory cytokines, then it can be presumed that whatever abnormality triggered the immune response has been successfully resolved. If, however, the presence of abnormal target cells, none of which are expressing anti-inflammatory cytokines, can be interpreted as the immune system entering a quiescent state due to having mounted an overly prolonged response, these results can indicate a moderately increased risk of progression.
4. The presence of both target and immune cells that are expressing anti-inflammatory cytokines is an indication that the immune system is being forcibly suppressed. This state indicates a high risk of progression to cancer.

Although clinically useful information can be obtained from these tests simply by noting whether any cells in a specimen are expressing an anti-inflammatory cytokine, it is more useful if the cells that are present are classified as to type at a level that at least differentiates between target and immune cells and, even more useful, if dysplastic and cancerous cells are morphologically detected and optionally classified.

Cytological specimens are obtained for purposes of risk assessment, not for clinical diagnosis. The specimens used in histological procedures are tissue slices where considerable reliance is placed upon the information contained in the three dimensional spatial relationships between the cells and intercellular materials of the tissue. Cytological specimens, on the other hand, consist of a two dimensional arrangement of dispersed cells in which the stroma and other intercellular materials present in a histological specimen have been removed, and the spatial relationships between the remaining cells have been intentionally disrupted. Due to this lack of intercellular material and the loss of spatial relationships, both of which are considered to be important in the classification and staging of dysplasias and cancers, cytological specimens are generally considered to be unsuited for use in the assessment of the risk of progression of cells to cancer. The methods disclosed herein are augmented to increase the value of cytological specimens.

A method for cytologically assessing the risk of dysplasia progressing to cancer includes:
(a) preparing a biological sample as a cytological specimen;
(b) detecting and classifying any dysplastic cells that are in the specimen;
(d) detecting the presence of an anti-inflammatory cytokine in any of the cells, normal or dysplastic, that are found in the specimen; and
(e) assessing (estimating) the risk of any dysplasia present in the subject from whom the sample was obtained, progressing to cancer, based upon whether an anti-inflammatory cytokine is present in dysplastic or other cells that may be in the specimen. A suitable anti-inflammatory cytokine for risk assessment is IL-10.

Dysplastic cells are stained with one or more fluorogenic stains and detected and classified on the basis of cell morphology. T-cells, B-cells, macrophages and/or other cells of the innate immune system are additionally detected and classified.

A method for the immunological determination of the spatial distribution of an analyte in a cytological specimen, is disclosed wherein the detection reagents include an antibody separately bearing a first and a second label. "Analyte" is used herein as whatever chemical or molecule is under analysis. This method is used, for example, to enhance signals of a cytokine (a) the first and second labeled antibody can specifically bind to the primary (unlabeled) antibody;
(b) the first and second labels exhibit different non-specific patterns of binding to the specimen;
(c) the first and second labels are individually detectable in a spatially resolved manner;

and the method further includes (d) optionally treating the specimen with an unlabeled primary antibody;
(e) treating the specimen with the first and second labeled antibody, the labeled antibodies being applied to the specimen concurrently;
(f) determining the locations on the specimen at which the first labeled antibody is bound;
(g) determining the locations on the specimen at which the second labeled antibody is bound; and
(h) spatially correlating the locations on the specimen at which the bound first and second labeled antibodies are present; wherein the analyte is deemed to be present at those locations where both the first and second labeled antibodies are present with high correlation, and the analyte is deemed to be absent at those locations where neither labeled antibody is present, or only one labeled antibody is present, or both labeled antibodies are present with low correlation.

The first and second labels may be fluorescent.

The specimen may further be treated with a fluorescent or fluorogenic morphological stain.

DETAILED DESCRIPTION

1. Clinical Rationale

Figure 1:
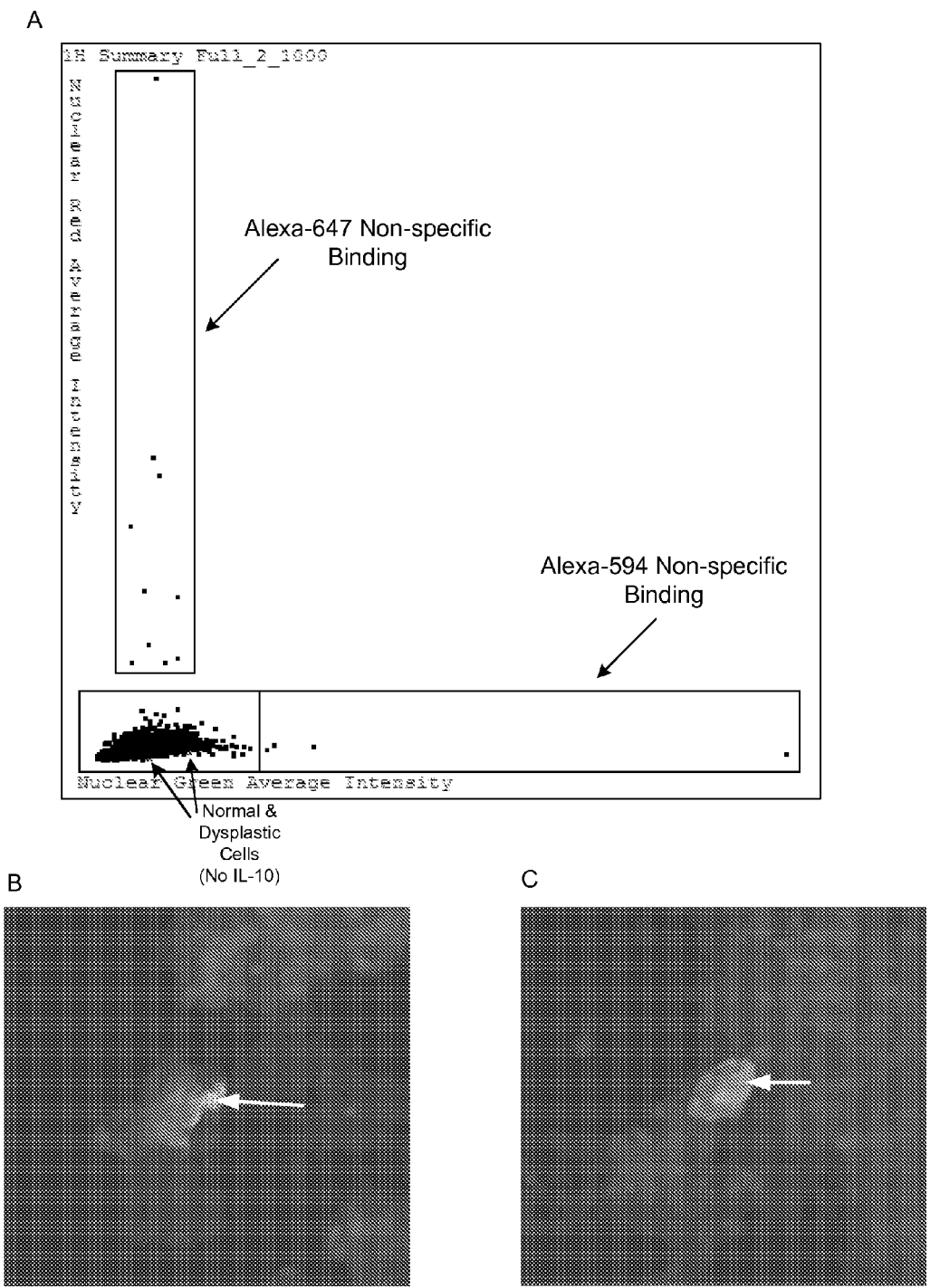
FIG. 1 shows results of IL-10 immunostaining on an IL-10 negative HSIL sample (D1H) with binding to antibodies Alexa-594® and Alexa-647®; (A) normal and dysplastic cells, scattergram (arrow points to red stained cells); (B) cell stained with Alexa-594® (green) NSB; R-G correlation coefficient=0.088; (C) cell stained with Alexa-647® (red) NSB; R-G correlation coefficient=0.67.

A method of using biological specimens to predict whether a patient is at an increased risk of developing cancer, is disclosed.

In the absence of cancer, infection or cellular damage that has evoked a repairative response, the cells in a cytological specimen will have morphologies that are within normal limits, and indicators of an immune response such as the presence of T-cells, B-cells and macrophages will be very rare. In a similar manner, a cell undergoing normal repair of damage unrelated to cancer or an infection will show morphological changes characteristic of the repair process and some macrophages may be present, but T-cells and B-cells will be absent. However, if cancer, a significant precancerous condition, or an infection is present, the cell will exhibit distinctive morphological changes and evidence of an active immune response in the form of effector T-cells, Th1 helper T-cells, M1 macrophages and possibly other effector cells of the innate immune system. An aborted immune response, on the other hand is marked by dysplasia in combination with Treg and (possibly) Breg cells, Th2 helper T-cells and M2 macrophages as well as production of anti-inflammatory cytokines. Hence, the production of an anti-inflammatory cytokine, such as IL-10, by these cells is an indication of an aborted immune response and is an indicator that the local environment is in an immunosuppressed state that is permissive of progression of the adverse condition.

From a clinical perspective, the detection of cancer cells in a cytological specimen is considered to warrant immediate confirmatory follow up and aggressive intervention, while the response to dysplastic (pre-cancerous) cells in these specimens is more likely to be based upon the clinician's assessment of the risk that the dysplasia will progress to cancer. Standards of care worldwide largely dictate that high grade dysplasia (HSIL) represents a high risk of progression and therefore warrants immediate intervention, while lesser degrees of dysplasia represent lower risks and are responded to accordingly. This risk assessment is, however, complicated by the fact that a small fraction of ASCUS and LSIL are known to progress and that a significant portion of HSIL (60-90% by some estimates) spontaneously regress. A means of more accurately assessing in cytological specimens the risk of progression in a subject from where the specimen was obtained; is therefore desirable. The presence of cells of any type, secreting IL-10, is indicative that the patient is at high risk for progression, and is independent of the degree of dysplasia and other risk factors such as infection by a high risk (oncogenic) strain of HPV.

The disclosed methods and compositions are primarily intended for risk assessment based upon the evaluation of cytological specimens in a cancer screening environment, but it may also be used with biopsy specimens and for diagnostic and patient management purposes. Touch preps are a particularly convenient form of biopsy specimen for this purpose, but other forms such as tissue slices and dispersed tissues may also be used. A cervical cytology sample such as is routinely used in cervical cancer screening will be assumed in the description below.

2. A Method of Predicting Risk that Dysplaysia Will Progress to Cancer

A method of predicting risk that dysplasia will progress to cancer includes:
 (a) detecting cytokines;
 (b) identifying dysplasia and cancerous cells; and
 (c) correlating the results of (a) and (b) into a classification used for risk evaluations.

A morphological stain is used in the detection of dysplastic and cancerous cells and immunological reagents for the detection of cytokines. Standard chromatic stains and chromatically labeled immunological reagents may be used for this purpose, but a fluorescent nuclear or morphological stain in combination with fluorescently-labeled immunological reagents is more convenient for most purposes. In particular, fluorescent staining facilitates concurrent or sequential staining of the same cell for multiple analytes whereas chromatic staining often necessitates applying each stain to a different specimen prepared from the same sample. Performing all staining on the same specimen greatly simplifies the correlation step and produces substantially more robust results.

A standard two step immunological staining procedure using a labeled secondary antibody is described, but other formats such as one using a labeled primary antibody may also be employed. Similarly, although this method may be performed using standard visual microscopy techniques, automated image capture in combination with automated analysis of these captured images is more convenient and effective, particularly when large numbers of specimens, such as are encountered in screening programs, must be evaluated.

DEFINITIONS

Screening as defined herein is the examination of a sample with the goal of detecting the presence of an abnormality. This translates to the detection of cells that are dysplastic. The operative word in this definition is "detecting". It says nothing about determining the specific type or cause of the dysplasia or what it signifies. A lot of the confusion surrounding this term stems from the common practice of also reporting a degree of dysplasia (none, low, medium, high) as part of the screening results.

Diagnosis, on the other hand, as defined herein has nothing to do with detection, but rather it focuses upon the detailed classification and the identification of the underlying cause of an already detected abnormality according to, for example, specific type, degree and other characteristics. As an example, a breast cancer screening result might be reported as atypical hyperplasia (the equivalent to high grade dysplasia in some other tissues) whereas the corresponding diagnosis may be might be stage 3 invasive ductal epithelial carcinoma further characterized as being negative or positive for a variety of cell surface markers such as ER, PR and Her2Neu (absence of all three of these indicates that the diagnosed cancer is of the infamous "triple negative" type).

EXAMPLES

The methods include the following steps. Certain of these steps may be omitted, combined, or performed in an order other than as presented depending upon the requirements of any particular use of this method.

In some cases it may be desirable to supplement this invention by the addition of steps in which the specimen is stained and evaluated for the presence of markers other than those included within the scope of this invention:

1. Obtaining a Cellular Sample.

Numerous cell collection devices and methods have been devised and their uses for the collection of cellular samples from tissues, body secretions, and other anatomical sources are well known in the art. Due to the diversity of such devices and methods that are available and because each such device or method is often intended for the collection of cells from some specific anatomical site, a detailed discussion of such devices and methods is beyond the scope of this description.

Any such device or method that is capable of collecting a sufficient number of the target cells may be used in the practice of this invention. Between 1000 and 5000 cells is generally sufficient, but a greater number is preferable particularly in cases where target cells are expected to comprise only a small subset of the total cells collected and/or when a significant loss of cells is anticipated during the preparation of a specimen from the sample.

Standard statistical methods may also be used to estimate the number of cells required to achieve a particular level of statistical confidence in the test result given an approximate value for the incidence rate of the disease state of interest in the population being tested. In addition to providing a sufficient number of target cells, the collection device and method preferably causes little if any damage to the collected cells, minimizes the collection of potentially interfering substances such as mucus and red blood cells, and satisfies various operational criteria related to ease of use, consistency, invasiveness, cost and similar factors. The target cells that are suitable for use in the practice of this invention are of epithelial origin. As available collection devices and methods are generally not highly selective as to the type of cell collected, non-target cells, which may be of epithelial or non-epithelial origin, are also present in the collected sample. The class of non-target cells that is of relevance to the practice of this invention are lymphocytes, comprising T-cells, B-cells, neutrophils, macrophages, myeloid-derived suppressor cells and other cells of the immune system.

In one preferred embodiment cervical epithelial cells may be collected using a cervical spatula or broom to scrape or abrade such cells from the surface of the cervix. In another preferred embodiment, a vacuum device is employed to cause the milk ducts in breast tissue to express a fluid (nipple aspirate fluid) containing ductal epithelial cells that are collected by absorption onto an absorbent material, filtration through a membrane filter, or by sedimentation Similarly, in other preferred, but not limiting embodiments, bladder cells may be collected from urine or bladder washings by filtration or sedimentation; lung cells may be collected from sputum; skin cells may be collected using any of a variety of scraping or adhesive devices and cells from tissues that are not directly accessible externally may be collected by fine needle aspiration (FNA). In some cases tissue samples obtained incidentally to a surgical procedure may be available. In such cases cells may be recovered from the tissue by dispersion of the tissue in a fluid medium or preferably by the touch prep method in which the surface of the tissue is brought into momentary contact with the surface of a microscope slide that has previously been coated with a material such as poly-L-lysine to which cells preferentially adhere. The samples collected by these and by other similar methods comprise mixtures of target and non-target cells.

Because collected cells are generally unstable and there is a potentially significant time delay between when the cells are collected and when they are prepared as specimens for evaluation, it is preferred that the freshly collected cells be preserved or fixed immediately after collection. Numerous formulations of preservatives and fixatives and equally numerous methods for their use are well known in the art. For the purposes of this invention the preferred preservative or fixative is alcohol-based or may alternatively be an organic solvent such as acetone or ether. Suitable alcohols include methanol, ethanol and iso-propanol either neat or more commonly in a buffered aqueous solution in which the alcohol concentration is between 15 and 80%. Suitable alcohol-based preservatives may additionally contain mucolytic and other modifying agents while alcohol-based fixatives often additionally contain a polymer such as Carbowax or poly-ethyleneglycol. Under some circumstances a cross-linking fixative such as ones comprising formaldehyde, formalin or glutaraldehyde may be used in the practice of this invention, but such fixatives are not preferred as the crosslinking reactions that occur in such fixatives can block, obscure or damage the epitopes that are to be detected in the immunostaining step of this invention.

2. Preparing a Cytological Specimen from the Cellular Sample.

The preparation of a cytological specimen requires that the collected cells be transferred to a microscope slide and then stained in a manner that highlights the cellular features and constituents of interest.

Numerous devices and methods for the deposition of cells onto a microscope slide are well known in the art and may be used in the practice of this invention. The preferred method is one that minimizes the number of cell clumps on the slide, the degree of overlap between adjacent cells on the slide, and the loss of cells and the damage done to cells during the transfer process. One such preferred method is cytocentrifugation in which the cells contained in a cell suspension are deposited onto a microscope slide under the influence of a centrifugal (gravitational) field. One limitation of this method is that contaminants such as mucus and red blood cells that may be present in the cell sample can be deposited on the slide in a manner that obscures target and non-target cells. In such cases the use of a cell preservative (see above) that contains suitable mucolytic and/or other selective lytic agents is appropriate. Alternatively, the removal of unwanted sample constituents by any of a variety of filtration or gradient centrifugation methods is widely practiced in the art. Such separations are an integral part of several widely used methods in which a membrane filter is used to transfer cells to the slide. Methods that utilize or incorporate cell separation may be used in the practice of this invention so long as the separation method does not result in an unacceptable degree of loss of target or non-target cells.

3. Treating the Cytological Specimen with One or More Morphological Stains.

As cells are visually transparent, it is necessary to treat the cells in a manner that establishes a detectable contrast between the cellular structures and other constituents of interest and their surroundings. This contrast is created by staining the cells with various reagents. The stains most commonly used in the evaluation of cytological specimens are chromatic stains such as hematoxylin, which stains DNA, and eosin, which stains various constituents of the cytoplasm. While these stains may be used separately, they are most commonly used in a combination that is often referred to as H&E stain. In some cases thionin is substituted for hematoxylin and/or other stains are combined with H&E for particular purposes. These conventional morphological stains can be used in the practice of this invention if this morphological staining is performed after the immunochemical staining procedure described below and a means such as recording the locations and identities of relevant morphologically identified target and non-target cells is provided in order to allow correlation of these morphological results with the results obtained from the immunochemical staining process described below.

Practice of the disclosed and claimed methods are greatly facilitated if the chromatic morphological stains such as H&E described above are replaced with fluorescent or fluorogenic morphological stains such as DAPI, POPRO and the like. The advantages of fluorescent staining over chromatic staining, especially when quantitative measurements of this staining are to be made, are well known in the art. Two of these advantages that are particularly pertinent to the present invention are that the wide range of concentrations of cellular constituents present in cells is more readily accommodated in fluorescence and fluorescent and fluorogenic morphological stains are more compatible with fluorescent immunostaining methods than are most chromatic stains. In the context of this last point, it should be noted that the chromatic stain eosin has a fluorescent emission that can overwhelm the emissions from most of the fluorophores commonly used in immunostaining procedures. For these reasons the use of fluorescent or fluorogenic morphological stains is strongly preferred in the practice of this invention. These fluorescent stains and their methods of use are well known in the art.

In certain cases it may be convenient or desirable to employ a cell-type selective immunological or other type of stain or stains in order to specifically detect target or non-target cells of interest. Examples of such selective staining include use of an immunostain comprising an anti-cytokeratin 19 primary antibody for the detection of ductal epithelial cells in a sample comprising nipple aspirate fluid, or the use of an anti-CD4 or anti-CD8 antibody for the detection and identification of specific classes of T-cells. Such selective staining methods and procedures are well known in the art.

4. Detecting, Identifying and Classifying Any Cells and Other Objects that May Be Present in the Cytological Specimen on the Basis of Morphology and Detecting the Presence of Target Cells Having Characteristics Indicative of Dysplasia, Cancer, Infection or Other Disease State on the Basis of Cell Morphology.

The methods and criteria for the morphological identification and classification of cells from various tissues are well known and established in the art. The identification and classification of target epithelial cells and of non-target cells of the immune system such as T-cells, B-cells, neutrophils, macrophages, and myeloid-derived suppressor cells is performed in the practice of this invention. Other types of cells may generally be ignored. Cell identification and classification is traditionally accomplished by the visual assessment of cell morphology, but it may also be beneficially accomplished by the automated analysis of electronically captured images of cells.

5. Treating the Cytological Specimen with One or More Immunological Stains and Detecting the Presence of One or More Anti-Inflammatory Cytokines.

Numerous methods for the immunostaining of cellular specimens for the purpose of detecting and optionally quantitating specific cellular constituents have been developed since this technique was first introduced in the 1950's. Of these, the "labeled secondary" and ELISA are formats are presently the dominant methods employed in the cytology laboratory. The "labeled secondary" format is the preferred immunostaining method in the practice of this invention. This format utilizes an unlabeled primary antibody that binds specifically to the cellular constituent of interest in combination with a fluorescently-labeled secondary antibody that binds specifically to the Fc portion of the primary antibody. Formats utilizing fluorescently-labeled primary antibody can also be used effectively, but can result in lower signal levels and can require custom labeling of the antibody.

Monoclonal primary antibodies that bind strongly and specifically to the anti-inflammatory cytokines TNF-$\beta$-I/II, IL-4, IL-6, IL-8, IL-10, IL-11, IL-13 and IL-19, either individually or in combination, are preferred for use in this invention. Of these, IL-10 has proven to be the most generally applicable to the detection of dysplasias that are likely to progress in a variety of tissues while the other anti-inflammatory cytokines such as IL-19 appear to be more tissue specific. The target cytokine or combination of cytokines is therefore best determined on the basis of the tissue from which the cell sample to be tested was obtained. All of the monoclonal antibody molecules produced by a particular clone are identical, but it is well known in the art that the specificities and affinities of these antibodies can vary widely between clones. Therefore, even if commercially available monoclonal antibodies are used, the performance of this invention will depend upon the particular antibodies and corresponding clones selected. Due to the relatively low concentrations of anti-inflammatory cytokines that are present in the samples used in this invention and the relatively low signal amplification available in the labeled secondary assay format, the preferred monoclonal primary antibodies should have affinities in the low nanomolar, or preferably the low to mid-picomolar range in combination with at least a moderately high specificity for the particular target cytokine.

The labeled secondary antibody is an antibody raised in a species other than the species of the primary antibody that binds specifically to the Fc portion of the selected primary antibody and to which several fluorophore molecules are attached. Suitable fluorescently labeled secondary antibodies are commercially available from numerous sources or may be prepared by methods that are well known in the art. A disadvantage of fluorophore-labeled secondary antibodies is that they exhibit a certain amount of non-specific binding, which makes rare event detection problematic. In the present invention this is overcome by the use of secondary antibodies labeled with fluorophores of different structural classes and hence different non-specific binding properties. Examples of such dyes are Alexa Fluor 594® and Alexa Fluor 647®.

Immunostaining of the specimen is carried out in the manner well known in the art by treating the specimen with the selected primary monoclonal antibody or antibodies specific for the target anti-inflammatory cytokines; removing unbound primary antibody by washing; treating the specimen with a mixture consisting of approximately equal parts of secondary antibody labeled with the first and second fluorophores; removing unbound secondary antibody by washing; and protecting the stained slide by the application of a coverslip.

The results of the immunostaining are assessed by examination of the stained specimen under a fluorescence microscope that has been configured to utilize excitation and emission wavelengths that are compatible with the first and second fluorophores employed. This assessment may be made visually or preferably by means of an automated image capture and analysis system. The intent of this assessment is to identify those cells, if any, present in the specimen where staining by the antibody labeled with the first fluorophore spatially coincides with staining by the antibody labeled with the second fluorophore. This procedure permits detection of and compensation for the non-specific binding of the labeled secondary antibody to the cells, which if uncorrected could yield false positive results. In general terms, if only one or the other of the labeled secondary antibodies is bound at a particular location on a cell it can be assumed that this binding is non-specific, but that if both labeled antibodies bind at the same location, the binding can be assumed to be specific and therefore a true indicator of the presence of the target anti-inflammatory cytokine.

6. Assessing the Relative Risk of the Target Cells Thus Identified Progressing to a More Adverse Disease State Based Upon the Detection of the Presence of One or More Anti-Inflammatory Cytokines in Some Portion of the Cells Comprising the Cytological Specimens.

In order to estimate the risk of progression it is necessary to classify each target and non-target cell, in which the immunostaining procedure of step 5 indicated that the target anti-inflammatory cytokine is expressed, in terms of its type and, if applicable, its degree of morphological abnormality. As immunostaining and morphological staining are performed on the same specimen, the immunostained cells detected in step 5 can be identified and classified based upon the morphological information pertaining to the same cell that was obtained in steps 3 and 4. This correlation may be performed manually, but is most conveniently performed using an automated image analysis system. It is also useful, but not necessary in the practice of this invention, to identify any unstained morphologically abnormal target cells and any unstained cells of the immune system that may be present.

The risk of progression can be stratified based upon the above information. These risks of progression are relative to the corresponding risk typically associated with a target cell of the same type that exhibits similar morphological characteristics, but which does not express an inflammatory cytokine.

An example of the results obtained by the above procedure is summarized in Table 1. Each sample was collected as part of the routine Papanicolaou (Pap) screening of women for the presence of cervical cancer or during follow up of women having a previous abnormal screening result. These samples were collected from the cervix through the use of a cervical spatula, sometimes in combination with an endocervical brush, and preserved in a commercially available methanol-based preservative (ThinPrep®). One portion of each sample was prepared as a cytological specimen; stained using the Pap stain; and morphologically evaluated by several trained cytologists in accordance with internationally accepted standards and criteria. The results from these conventional cytological evaluations of this portion of the sample are recorded in the "Cytology" column of Table 1, which is organized by increasingly adverse cytological diagnosis, and comprise the official reference diagnoses for these specimens. HPV status is also provided where available as infection with a high risk (HR, oncogenic) strain of the HPV virus is widely considered to be a primary cause of cervical cancer. Infection or co-infection by low risk (LR, non-oncogenic) strains of HPV are also noted when available.

A second portion of each sample comprising approximately 5000 total cells was prepared by cytocentrifugation; stained using POPRO; immunostained using a rabbit monoclonal anti-IL-10 primary antibody in combination with goat-anti-rabbit secondary antibodies labeled with Alexa Fluor 594® and Alexa Fluor 647®. Morphological evaluation, data capture and data analysis were performed both visually using a commercially available fluorescence microscope (Olympus BX-50) and using a custom-built automated image capture and analysis system. The correlation between IL-10 staining and morphological classification is shown in the "HSIL" and "HSIL Group" columns in Table 1. In this particular study a reporting threshold of HSIL was used as this level of morphological abnormality is often considered to be the threshold for initiating aggressive patient follow up. HSIL and HSIL Groups are reported separately as HSIL Groups are often considered to be a more adverse result than is HSIL in isolated cells. The "Risk Assessment column identifies the morphological classification(s) of any IL-10 expressing squamous epithelial cells and the corresponding estimated level of risk that the patient was likely to progress to a more adverse disease state than indicated in the "Cytology" column.

Sample 10 in Table 1 indicates the ability of this invention to detect the presence of abnormal cells in a nominally "normal" sample. In this specific instance both IL-10 positive isolated HSIL and a clump of IL-10 positive HSIL were found. Thus although this sample was reported as being normal by conventional cytology, this patient should be considered as being at high risk of progression to cancer.

Sample 15 in Table 1 is classified as ASCUS by conventional cytology. ASCUS is a category that is used predominantly in the US to denote the presence of squamous cells exhibiting morphological abnormalities that do not fall within the traditional categories of LSIL, HSIL or Cancer. It is thought that at least some fraction of samples reported as ASCUS represent sample collection errors in which the sample was collected from an area adjacent to, rather than including, a lesion that if properly sampled would return a diagnosis of LSIL or higher. As a significant portion of the abnormal results reported during the Pap screening for cervical cancer are classified as ASCUS, a method for identifying that subset of ASCUS samples that are clinically significant is desirable. This particular sample was found to contain IL-10 expressing cells that upon morphological evaluation were found to be HSIL or HSIL clumps and that the patient should therefore be considered to be at a high risk of progression.

Under the Bethesda System for the classification of cells in cervical cancer screening LSIL (samples 16-42 in Table 1) is a heterogeneous category that includes both cells exhibiting the morphological changes associated with low grade dysplasia and cells that exhibit the morphological changes associated with infection of cells by viruses such as HPV. It is well known in the art that a significant fraction, over 90% by many estimates, of cells classified as LSIL will spontaneously revert to normal over time while the remainder will progress to HSIL. As is the case for ASCUS, these considerations indicate that a means of identifying that subset of LSIL samples that are likely to progress is desirable. LSIL samples 16-34 in Table 1 do not contain IL-10 expressing squamous epithelial cells and are therefore not considered to be at an increased risk of progression while LSIL samples 35-42 are positive for IL-10 progression and were found to contain HSIL and/or HSIL groups upon reexamination. It is of interest to note that cells that were morphologically classified as LSIL did not express IL-10. Another factor of note is that some of these LSIL samples, including sample 41 which was judged to be at high risk of progression, tested negative for the presence of High Risk HPV infection. This type of observation has implications for the proposed use of HPV testing as the primary means of cervical cancer screening.

As is the case for LSIL, a certain portion of cases classified as HSIL are known to spontaneously revert to normal while the remaining cases progress to cancer. This portion of cases that spontaneously regress has been variously estimated as being between 30 and 60%. The lack of IL-10 expression reported for samples 43-47 suggests that these samples are likely to regress whereas samples 48-63 express IL-10 and are likely to progress if not treated.

In addition to the embodiment described above, steps may vary depending upon the requirements of a specific application. For example, the order of steps 4/5 and step 6 may be reversed or, is a fluorescent or fluorogenic morphological stain is used, these steps can be combined into a single step. Similarly, morphological staining and evaluation can be performed only on those specimens on which evidence of immunostaining for the presence of anti-inflammatory cytokines are noted or morphological staining and evaluation can be deleted entirely and the presence or absence of staining for an anti-inflammatory cytokine can be taken as the indicator of whether additional follow up is required. This invention can also be extended by performing staining and evaluation for the presence of additional markers such as PD-1, PD-L1, CTLA-4, p-16, and Ki-67 in order to obtain additional information about a particular specimen.

7. Obtain a Suitable Sample.

In the case of cervical cancer screening, this sample traditionally comprises primarily epithelial cells that are obtained from the cervix by scraping or brushing, but also contains other cell types that are present in the tissue sampled.

8. Prepare a Cytological Specimen from the Sample.

Cytology specimens for cervical cancer screening are traditionally prepared by using the cell collection device to physically smear the collected cells onto a microscope slide. Specimens prepared in this manner may be used with the caveat that some cells of interest may be embedded in clumps or clusters or otherwise obscured and therefore not readily evaluated.

The "monolayer" or "liquid based" method of specimen preparation was introduced in large measure to address the obscuration issues inherent in smear type preparations. In these methods the collected cells are washed from the cell collection device into a liquid medium thereby forming a cell suspension. The cells contained in this suspension are then deposited onto a microscope slide by any of several established means.

Capture of the suspended cells on the surface of a membrane filter, followed by either placing the filter with captured cells on a microscope slide, or transferring the captured cells from the filter to a microscope slide, includes one of the two major classes of such methods that are in widespread use. Specimens prepared in this manner can be used provided that a suitable filter is used. The filters most commonly used in preparing specimens for cervical cancer screening are designed to capture, on the surface of the filter, the epithelial cells that are traditionally evaluated, while allowing other cell types that may be present in the sample, including T-cells, macrophages and other types employed in the practice of this invention, to pass through the filter and into a waste container. Unless a filter having smaller pores and being capable of capturing T-cells, macrophages and other types of cells employed in the practice of this method is used, the numbers of these cells in the resulting specimens will be significantly reduced relative to their numbers in the original sample.

The other commonly practiced method of preparing specimens from cell suspensions relies upon the settling of the cells in the suspension onto a microscope slide in the presence of a gravitational field. Methods in which this settling occurs in a 1×G field and methods in which this field is increased to several hundred ×G by, for example by centrifugation (e.g., a CytoSpin®) are commonly employed and may be used. However, the specific version of the settling method that has received regulatory approval for use in the preparation of specimens for cervical cancer screening requires that the sample be separated into an epithelial cell fraction and a fraction containing the other types of cells present in the sample, and that only the epithelial cell fraction be deposited onto the slide for cytological evaluation. As in the case of the filtration method described above, the numbers of T-cells, macrophages and other types of cells that are present on a slide prepared by this approved method will be significantly reduced relative to their numbers in the original sample. For this reason it is preferred in the practice of this invention that fractionation of the sample prior to deposition be omitted. Alternatively, the fractions containing the epithelial and other types of cells can be separately recovered and evaluated.

9. Detect and Optionally Classify Any Dysplastic and/or Cancerous Cells that May Be Present in the Specimen.

The morphology based cytological detection and classification of dysplastic and cancerous cells is carried out in accordance with internationally accepted practices and standards. In these practices detection and classification is facilitated by staining the specimen prior to examination. The Pap stain is commonly used in the screening of cervical cytology specimens while H&E with or without various counterstains is typically used with other types of specimens. These and other stains may be used.

The cytology classification reported traditionally applies to the entire specimen. A specimen level result can be used, but it is preferable that each cell detected in the specimen be individually classified. An automated image capture and analysis system is a convenient means of providing this function.

The results of this classification are reported in accordance with any of several standardized systems of nomenclature. The major reporting categories in the widely used Bethesda nomenclature system and corresponding follow up practices are:

Within Normal Limits (WNL, typically also includes reactive and repairative)
  No follow up or intervention warranted.
Low grade Dysplasia (LSIL)
  Between 90 and 95% of all LSIL spontaneously revert to WNL as the lesion is cleared by the immune system. Local standards of care generally do not recommend follow up other than a shortened interval between screenings unless other risk factors are present.
High Grade Dysplasia (HSIL)
  Standards of care dictate therapeutic intervention if HSIL is confirmed by biopsy. Between 60 and 90% of all HSIL are spontaneously cleared by the immune system with the balance progressing to cancer.
Cancer (CA)
  Immediate therapeutic intervention if CA is confirmed by biopsy.
Atypical Squamous Cells of Undetermined Significance (ASCUS—recognized in some countries)
  The large majority of ASCUS findings are determined to be benign on follow up, but a small percentage are suggestive or indicative of HSIL or CA. Follow up is generally determined on a case-by-case basis.

As can be seen from the foregoing, although the present invention can be applied to specimens in any of these categories, it is most beneficial when applied to specimens that are classified as being HSIL or ASCUS on the basis of morphology and to LSIL specimens if other risk factors are present.

10. Detect the Presence of an Anti-Inflammatory Cytokine in Any of the Dysplastic Cells, Regulatory T-Cells, Regulatory B-Cells and M2 Macrophages in the Specimen.

Interleukin 10 (IL-10) is the preferred anti-inflammatory cytokine for the present method because IL-10 plays a central role in terminating the local immune response and has been shown, at least in some cancers, to be involved in other progression events such as suppression of apoptosis and reduction of the display of tumor antigens on the MHC-I complex. Other anti-inflammatory cytokines such as TNF-β may also be used. Detection of these cytokines is most conveniently accomplished by immunostaining. Any standard method of immunostaining can be used. The preferred immunostaining format utilizes an unlabeled primary antibody in combination with a fluorescently-labeled secondary antibody. Formats utilizing fluorescently-labeled primary antibody can also be used effectively, but can result in lower signal levels and can require custom labeling of the antibody.

11. Assessing the Risk that the Dysplasia in the Patient from Whom the Specimen was Obtained Will Progress to Cancer.

It is assumed that the specimens evaluated by this method predominately includes HSIL plus selected subsets of LSIL and ASCUS in which the patient has additional recognized classical risk factors such as a family or personal history of cancer, DES exposure, or a persistent infection by an oncogenic virus (such as a high risk strain of HPV).

The presence of an anti-inflammatory cytokine, such as IL-10, in any cell in the specimen can be taken as evidence that the local immune response is being, or has been terminated. If expression of an anti-inflammatory cytokine such as IL-10 is not detected in the dysplastic cells in the specimen, it is reasonable to assume that this termination is a normal response to prolonged stimulation of the immune system. As the dysplasia is still present, there is a moderate risk of progression.

The presence of dysplastic cells expressing an anti-inflammatory cytokine such as IL-10 can be taken as evidence that the local immune response is being actively suppressed and that the patient is therefore at a high risk of progressing to cancer, especially if regulatory cells are also present.

Discussion

It is not unusual for cells expressing an anti-inflammatory cytokine such as IL-10 to be rare, even in specimens that are classified as HSIL and cancer on the basis of morphology. This is largely due to the use of the traditional cell collection methods which generally collect T-cells, macrophages and other cells of the immune system only incidentally to the collection of the targeted cell type. Because it is often desirable, if not necessary, to employ samples collected using these traditional methods to produce the method disclosed and claimed herein, it is necessary to optimize the immunostaining reagents and methods to maximize detection of the target cell types. A wide variety of optimization techniques are well established in the art and can be used. However, fluorophores such as those used in the practice of this invention are known to have tendencies toward binding non-specifically to cellular constituents in a manner that is not effectively controlled by standard optimization techniques. For this reason, another aspect of the present invention is directed toward mitigating the effects of this non-specific binding on the sensitivity of the test.

Non-specific binding in immunoassays is addressed by the use of various combinations of blocking agents, detergents, chaotropic agents and other additives. Although these methods are generally effective in limiting or suppressing most types of non-specific binding, their effectiveness in mitigating the non-specific binding of fluorophores to cellular constituents is not adequate for the practice of this invention. The present method therefore uses correlated double staining to address this deficiency.

The previously described immunostaining format including an unlabeled primary antibody in conjunction with a labeled secondary antibody is used in this description. It is further assumed that the label is a fluorophore selected from the widely used Alexa® series. When used in the tests of the present method it can readily be observed that different members of the Alexa® series exhibit different patterns of non-specific binding to cellular material. Thus the observed staining pattern includes the superposition of the specific staining of the target analyte and the non-specific binding of the fluorophore to the cellular material. If a different fluorophore is used as a label, the analyte specific staining pattern will remain the same while the pattern due to non-specific binding of the fluorophore will change. This consistency in analyte specific staining in combination with the variability in fluorophore specific non-specific staining provides a method of minimizing the effect of non-specific fluorophore binding on the analytical result.

Correlated double staining utilizes two aliquots of the same secondary antibody, one of which is labeled with a first fluorophore and the second of which is labeled with a second fluorophore. By way of example, the first aliquot is labeled with Alexa-647®, which has a fluorescent emission in the near infra-red spectral region, and the second is labeled with Alexa-594® which has a fluorescent emission in the red spectral region. These two labeled secondary antibodies are combined before use.

As previously described, the specimen is first treated with an unlabeled primary antibody that binds specifically to the analyte of interest. The specimen is then treated with the combined labeled secondary antibodies and images of the specimen are captured in both the red and infra-red spectral regions. These red and infra-red images are then correlated to identify those regions of the specimen in which the analyte is present.

If, for a given area, a low signal is detected in both the red and infra-red images, no staining has occurred at the corresponding location in the specimen and the target analyte is not present at that location.

If, for a given area, a high signal is detected in both the red and infra-red images, and the signals are correlated, the corresponding location in the specimen has been stained selectively and the analyte is present at that location.

If, for a given area, a high signal is detected in either the red or the infra-red image, but not in both, the corresponding location in the specimen has been stained non-specifically and the analyte is not present at that location.

FIG. 1 is a scattergram that shows results of IL-10 immunostaining of an IL-10 negative HSIL sample. The detection reagents consist of a primary antibody specific for IL-10 and a mixture consisting of a secondary antibody labeled with Alexa-594® (green fluorescence) and the same secondary antibody labeled with Alexa-647® (red fluorescence) FIG. 1(B): Cells exhibiting low spatial correlation (R-G Correlation Coefficient=0.088) between red and green fluorescence thus indicating non-specific binding of the secondary antibodies. The predominantly red fluorescence indicates that these cells non-specifically bind the Alexa-647® labeled secondary antibody preferentially over the secondary antibody labeled with Alexa-594®. FIG. 1(A):

Morphologically normal and abnormal cells exhibiting high spatial correlation (R-G Correlation Coefficient>0.9) between red and green fluorescence. This indicates that both labeled secondary antibodies are bound specifically. The low fluorescence intensities in this region indicate that little or no IL-10 is present in either morphologically normal (black squares) or dysplastic (red squares). FIG. 1(C): Cells exhibiting low spatial correlation (R-G Correlation Coefficient=0.67) between red and green fluorescence thus indicating non-specific binding of the secondary antibodies. The predominantly green fluorescence indicates that these cells non-specifically bind the Alexa-594® labeled secondary antibody preferentially over the secondary antibody labeled with Alexa-647®.

Figure 2:
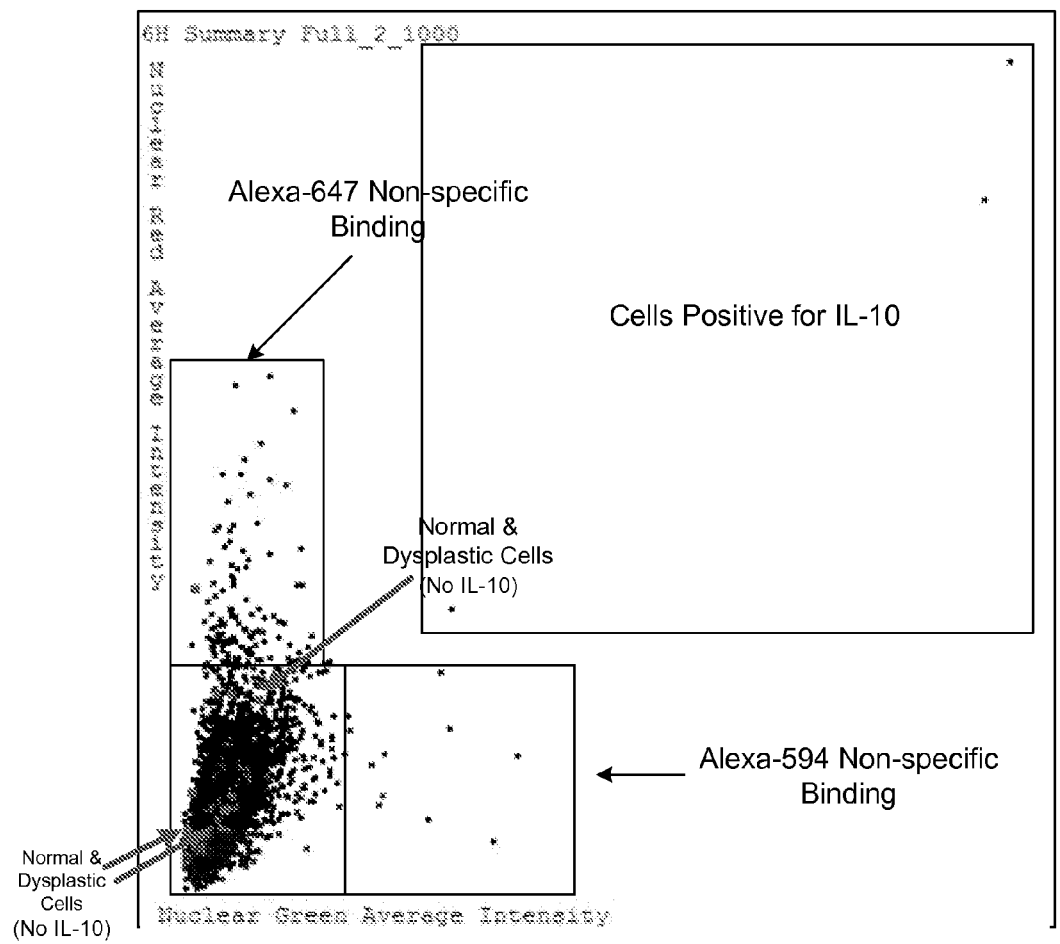
FIG. 2 is a scattergram showing results of IL-10 immunostaining on an IL-10 positive HSIL sample (D6H) with binding to antibodies Alexa-647® and Alexa-594®; normal and dysplastic cells (arrow points to red stained cells).
Figure 3A:
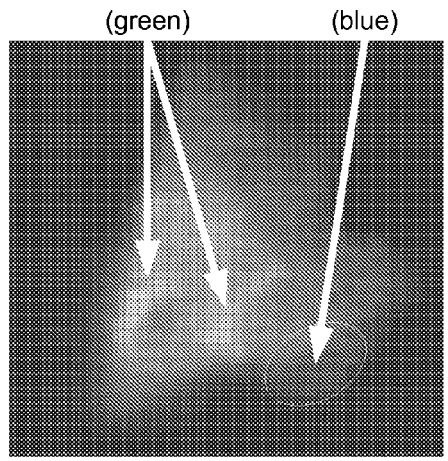
FIG. 3 shows pseudocolor images of cells: (A), (B) wherein non-specific binding was illustrated by color separated images of the same cell showing poor spatial correlation (<0.08) of the localization of (A) the Alexa-594® (green) and (B) Alexa-647® (red) labeled secondary antibodies. Blue denotes staining of the cell nucleus by DAPI; (C), (D), (E) shows specific binding of (C) IL-10 positive HSIL clump; (D) HSIL clump—594 stain; (E) HSIL clump—647 stain; (F), (G), (H) shows specific binding of (F) IL-10 lymphocyte; (G) IL-10 lymphocyte—594 stain; (H) IL-10 lymphocyte—647 stain.
Figure 3B:
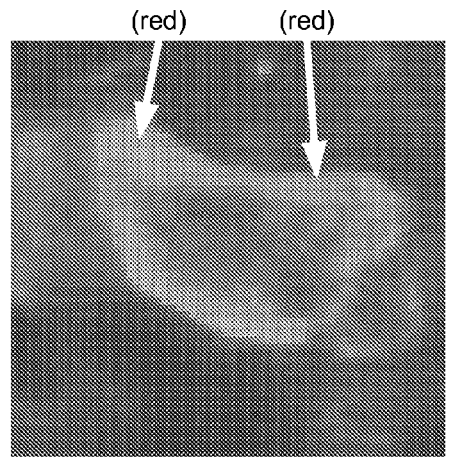
Figure 3C:
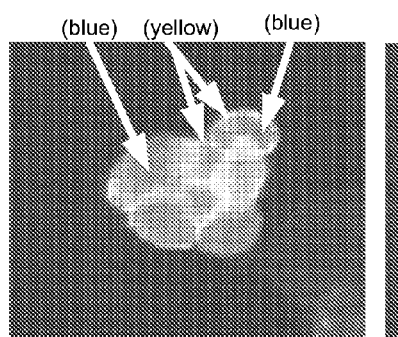
Figure 3D:
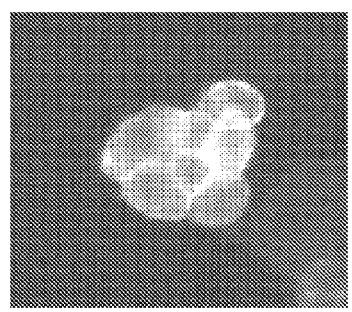
Figure 3E:
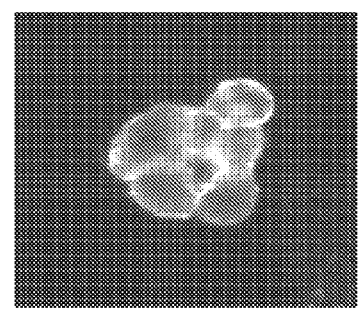
Figure 3F:
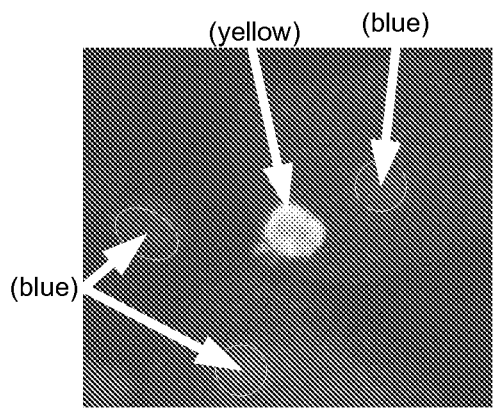
Figure 3G:
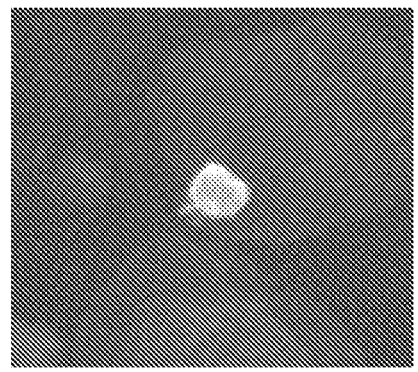
Figure 3H:
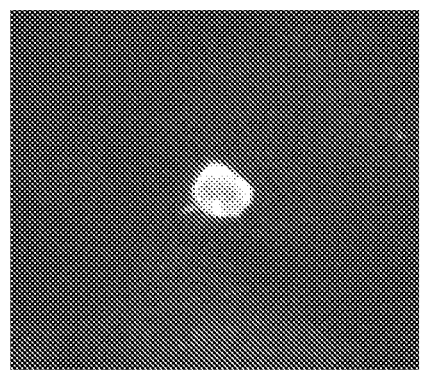

FIG. 2 is a scattergram that shows results of IL-10 immunostaining of an IL-10 positive HSIL sample. Staining of these cells and the interpretation of are as described in the legend for FIG. 1. Cells exhibiting both high red and green fluorescence intensities indicate strong IL-10 production and high spatial correlation (R-G Correlation Coefficient>0.9) between red and green fluorescence indicating that binding of the secondary antibodies is specific.

FIG. 3 shows color separated images of the same cell showing strong (>0.90) spatial correlation of the localization of the Alexa-594® (green) and Alexa-647® (red) labeled secondary antibodies. Blue denotes staining of the cell nucleus by DAPI. Co-localized red and green emission appears as yellow in this image. Color separated images of the same cell showing strong (>0.90) spatial correlation of the localization of the Alexa-594® (green) and Alexa-647® (red) labeled secondary antibodies. Blue denotes staining of the cell nucleus by DAPI. Co-localized red and green emission appears as yellow in this image. IL-10 negative cells in this image set are indicated by blue nuclei in a green surround (non-specific binding of the Alexa 594 labeled secondary antibody).

TABLE 1

| Sample | Cytology | HPV Status | IL-10 positive HSILs | IL-10 positive HSIL Groups | Dysplasias Found and Risk Assessment |
|---|---|---|---|---|---|
| 1 | Normal | Unknown | Negative | Negative | Normal risk |
| 2 | Normal | Unknown | Negative | Negative | Normal risk |
| 3 | Normal | Unknown | Negative | Negative | Normal risk |
| 4 | Normal | Unknown | Negative | Negative | Normal risk |
| 5 | Normal | Unknown | Negative | Negative | Normal risk |
| 6 | Normal | Unknown | Negative | Negative | Normal risk |
| 7 | Normal | Unknown | Negative | Negative | Normal risk |
| 8 | Normal | Unknown | Negative | Negative | Normal risk |
| 9 | Normal | Unknown | Negative | Negative | Normal risk |
| 10 | Normal | Unknown | Positive | Positive | HSIL. High risk for progression |
| 11 | ASCUS | Positive | Negative | Negative | Normal risk |
| 12 | ASCUS | Negative | Negative | Negative | Normal risk |
| 13 | ASCUS | Negative | Negative | Negative | Normal risk |
| 14 | ASCUS | Positive | Negative | Negative | Normal risk |
| 15 | ASCUS | Positive | Positive | Positive | HSIL. High risk for progression |
| 16 | LSIL | Positive | Negative | Negative | Normal risk |
| 17 | LSIL | Positive | Negative | Negative | Normal risk |
| 18 | LSIL | Positive | Negative | Negative | Normal risk |
| 19 | LSIL | LR Positive | Negative | Negative | Normal risk |
| 20 | LSIL | Negative | Negative | Negative | Normal risk |
| 21 | LSIL | HR Positive | Negative | Negative | Normal risk |
| 22 | LSIL | HR, LR Positive | Negative | Negative | Normal risk |
| 23 | LSIL | HR, LR Positive | Negative | Negative | Normal risk |
| 24 | LSIL | LR Positive | Negative | Negative | Normal risk |
| 25 | LSIL | HR Positive | Negative | Negative | Normal risk |
| 26 | LSIL | HR Positive | Negative | Negative | Normal risk |
| 27 | LSIL | HR Positive | Negative | Negative | Normal risk |
| 28 | LSIL | HR Positive | Negative | Negative | Normal risk |
| 29 | LSIL | Negative | Negative | Negative | Normal risk |
| 30 | LSIL | HR Positive | Negative | Negative | Normal risk |
| 31 | LSIL | HR Positive | Negative | Negative | Normal risk |
| 32 | LSIL | HR, LR Positive | Negative | Negative | Normal risk |
| 33 | LSIL | HR Positive | Negative | Negative | Normal risk |
| 34 | LSIL | HR Positive | Negative | Negative | Normal risk |
| 35 | LSIL | HR Positive | Negative | Positive | LSIL-HSIL. High risk for progression |
| 36 | LSIL | Positive | Positive | Negative | LSIL-HSIL. High risk for progression |
| 37 | LSIL | HR Positive | Positive | Negative | LSIL-HSIL. High risk for progression |
| 38 | LSIL | HR Positive | Positive | Negative | LSIL-HSIL. High risk for progression |
| 39 | LSIL | HR, LR Positive | Positive | Negative | LSIL-HSIL. High risk for progression |
| 40 | LSIL | HR Positive | Positive | Negative | LSIL-HSIL. High risk for progression |
| 41 | LSIL | Negative | Positive | Positive | LSIL-HSIL. High risk for progression |
| 42 | LSIL | HR, LR Positive | Positive | Positive | LSIL-HSIL. High risk for progression |

TABLE 1-continued

| Sample | Cytology | HPV Status | IL-10 positive HSILs | IL-10 positive HSIL Groups | Dysplasias Found and Risk Assessment |
|---|---|---|---|---|---|
| 43 | HSIL | HR Positive | Negative | Negative | Moderate risk for progression |
| 44 | HSIL | HR Positive | Negative | Negative | Moderate risk for progression |
| 45 | HSIL | HR Positive | Negative | Negative | Moderate risk for progression |
| 46 | HSIL | HR Positive | Negative | Negative | Moderate risk for progression |
| 47 | HSIL | HR Positive | Negative | Negative | Moderate risk for progression |
| 48 | HSIL | Positive | Negative | Positive | High risk for progression |
| 49 | HSIL | Unknown | Negative | Positive | High risk for progression |
| 50 | HSIL | HR Positive | Negative | Positive | High risk for progression |
| 51 | HSIL | Unknown | Positive | Negative | High risk for progression |
| 52 | HSIL | Unknown | Positive | Negative | High risk for progression |
| 53 | HSIL | Unknown | Positive | Negative | High risk for progression |
| 54 | HSIL | Unknown | Positive | Negative | High risk for progression |
| 55 | HSIL | HR Positive | Positive | Negative | High risk for progression |
| 56 | HSIL | HR Positive | Positive | Negative | High risk for progression |
| 57 | HSIL | HR Positive | Positive | Negative | High risk for progression |
| 58 | HSIL | Positive | Positive | Positive | High risk for progression |
| 59 | HSIL | Unknown | Positive | Positive | High risk for progression |
| 60 | HSIL | Unknown | Positive | Positive | High risk for progression |
| 61 | HSIL | Unknown | Positive | Positive | High risk for progression |
| 62 | HSIL | HR Positive | Positive | Positive | High risk for progression |
| 63 | HSIL | HR Positive | Positive | Positive | High risk for progression |

We claim:

1. A method for estimating the risk of dysplasia progressing to a higher degree of dysplasia or to cancer in a subject, the method comprising:
   (a) determining whether one or more anti-inflammatory cytokines are present in a cytological preparation of a biological sample comprising cells from the subject;
   (b) morphologically classifying each cell in which it is determined that one or more anti-inflammatory cytokines is present, as an epithelial cell, a cell type of the innate immune system, or another type of cell;
   (c) further morphologically classifying each epithelial cell in which one or more anti-inflammatory cytokines are present as non-dysplastic, dysplastic or cancerous;
   (d) sub-classifying dysplastic epithelial cells according to the degree of dysplasia present and/or optionally sub-classifying cells of the innate immune system by cell type;
   (e) estimating the risk of dysplasia progressing to a higher degree of dysplasia or to cancer based upon whether at least one anti-inflammatory cytokine is present in dysplastic cells and/or cells of the innate immune system according to:
   where: WNL =non-dysplastic epithelial cell;
   DYSP=dysplastic epithelial cell; and
   IMM=cell of the immune system;
   and the risk is inferred from the following table:

| Cell Class | Cytokine Present | Cell Class | Cytokine Present | Risk of Progression |
|---|---|---|---|---|
| WNL | No | IMM | No | Normal State |
| WNL | No | IMM | Yes | Moderate Increased Risk |
| DYSP | No | IMM | No | Slightly Increased Risk |
| DYSP | No | IMM | Yes | Moderately Increased Risk |
| DYSP | Yes | IMM | Yes | Greatly Increased Risk | wherein the presence of anti-inflammatory cytokines is determined using an immunofluorescence method comprising an unlabeled primary antibody and two identical secondary antibodies, wherein each antibody is labeled with a different fluorophore.

2. A method for the immunological determination of the spatial distribution of an analyte in a cytological or histological specimen, the method comprising:

a. contacting the specimen with an unlabeled primary antibody;

b. contacting the specimen with a reagent comprising two identical secondary antibodies wherein each antibody is labeled with a different fluorophore, and wherein the labeled secondary antibodies are bound to the specimen;

c. determining the locations on the specimen where the two labeled secondary antibodies are bound;

d. spatially correlating the locations on the specimen at which the bound first and second labeled secondary antibodies are present, wherein the analyte is inferred present at the locations where both the first and second labeled secondary antibodies are present, and the analyte is inferred to be absent where neither labeled secondary antibody is present, only one labeled secondary antibody is present, or both labeled secondary antibodies are present with low correlation, wherein the cells in the specimen are contacted with a fluorescent or fluorogenic morphological stain and identified and/or classified morphologically.

3. The method of claim 2 wherein the analyte is an anti-inflammatory cytokine and the unlabeled primary antibody is an antibody that selectivity binds to an anti-inflammatory cytokine.

* * * * *